United States Patent
Grewe

(10) Patent No.: US 9,782,247 B2
(45) Date of Patent: Oct. 10, 2017

(54) FLEXIBLE EMBOLIC DOUBLE FILTER

(71) Applicant: Cook Medical Technologies LLC, Bloomington, IN (US)

(72) Inventor: David D. Grewe, West Lafayette, IN (US)

(73) Assignee: Cook Medical Technologies, LLC, Bloomington, IN (US)

( * ) Notice: Subject to any disclaimer, the term of this patent is extended or adjusted under 35 U.S.C. 154(b) by 205 days.

(21) Appl. No.: 14/570,348

(22) Filed: Dec. 15, 2014

(65) Prior Publication Data

US 2015/0230907 A1    Aug. 20, 2015

Related U.S. Application Data

(60) Provisional application No. 61/940,879, filed on Feb. 18, 2014.

(51) Int. Cl.
*A61F 2/01* (2006.01)

(52) U.S. Cl.
CPC .......... *A61F 2/01* (2013.01); *A61F 2002/011* (2013.01); *A61F 2002/018* (2013.01); *A61F 2230/0006* (2013.01); *A61F 2230/0008* (2013.01); *A61F 2230/0067* (2013.01); *A61F 2230/0069* (2013.01); *A61F 2250/0023* (2013.01); *A61F 2250/0031* (2013.01)

(58) Field of Classification Search
CPC ...... A61F 2/013; A61F 2/01; A61F 2002/016; A61F 2250/0023; A61F 2250/0014
See application file for complete search history.

(56) References Cited

U.S. PATENT DOCUMENTS

| | | | |
|---|---|---|---|
| 6,375,560 B1 * | 4/2002 | Verrijp | A22C 21/0007 452/187 |
| 6,638,294 B1 * | 10/2003 | Palmer | A61F 2/013 606/200 |
| 2001/0025187 A1 * | 9/2001 | Okada | A61F 2/01 606/200 |
| 2001/0031982 A1 | 10/2001 | Peterson et al. | |
| 2001/0044634 A1 | 11/2001 | Don Michael et al. | |
| 2002/0004667 A1 * | 1/2002 | Adams | A61F 2/013 606/200 |
| 2002/0052627 A1 * | 5/2002 | Boylan | A61F 2/013 606/200 |

(Continued)

FOREIGN PATENT DOCUMENTS

WO    0158382    8/2001

OTHER PUBLICATIONS

Yi-Ling Lu, Ben-Xia Yang, Zong-Ning Yin; Immunotargeting of Collagenase on Thrombus; International Journal of Nanomedicine; 2010:5; pp. 973-982; West China School of Pharmacy, Sichuan University, Chengdu, Sichuan 610041, People's Republic of China.

(Continued)

*Primary Examiner* — Christopher L Templeton
(74) *Attorney, Agent, or Firm* — Liell & McNeil

(57) ABSTRACT

An intraluminal filtration device for embolic protection includes a device body and each of a coarse filter and a fine filter, for filtering larger-size and smaller-size particles, respectively. The device body includes a body wall extending circumferentially around the longitudinal axis, and being formed at least in part of an organic gel.

17 Claims, 3 Drawing Sheets

(56) References Cited

U.S. PATENT DOCUMENTS

| | | | |
|---|---|---|---|
| 2002/0062133 A1* | 5/2002 | Gilson | A61F 2/01 606/200 |
| 2002/0072730 A1* | 6/2002 | McGill | A61F 2/013 604/525 |
| 2002/0138094 A1* | 9/2002 | Borillo | A61F 2/013 606/200 |
| 2002/0161389 A1* | 10/2002 | Boyle | A61F 2/013 606/200 |
| 2003/0032977 A1* | 2/2003 | Brady | A61F 2/01 606/200 |
| 2003/0130680 A1* | 7/2003 | Russell | A61F 2/01 606/200 |
| 2003/0139802 A1 | 7/2003 | Wulfman et al. | |
| 2004/0088001 A1* | 5/2004 | Bosma | A61F 2/01 606/200 |
| 2004/0093010 A1* | 5/2004 | Gesswein | A61F 2/013 606/200 |
| 2004/0093012 A1* | 5/2004 | Cully | A61F 2/013 606/200 |
| 2004/0093015 A1 | 5/2004 | Ogle | |
| 2004/0158275 A1* | 8/2004 | Crank | A61F 2/013 606/200 |
| 2005/0021152 A1 | 1/2005 | Ogle et al. | |
| 2005/0096692 A1* | 5/2005 | Linder | A61F 2/013 606/200 |
| 2005/0124876 A1* | 6/2005 | Douk | A61B 17/221 600/431 |
| 2005/0177186 A1* | 8/2005 | Cully | A61F 2/013 606/200 |
| 2005/0234501 A1* | 10/2005 | Barone | A61F 2/01 606/200 |
| 2007/0088383 A1 | 4/2007 | Pal et al. | |
| 2007/0191877 A1* | 8/2007 | Dinh | A61F 2/013 606/200 |
| 2008/0058760 A1* | 3/2008 | Agerup | A61K 9/0048 604/521 |
| 2008/0208245 A1 | 8/2008 | Hoffman | |
| 2008/0208310 A1* | 8/2008 | McDermott | A61F 2/86 623/1.11 |
| 2009/0138035 A1* | 5/2009 | Isshiki | A61F 2/01 606/200 |
| 2009/0187210 A1 | 7/2009 | Mackiewicz | |
| 2010/0152829 A1* | 6/2010 | Edelman | A61F 2/013 623/1.11 |
| 2010/0185229 A1 | 7/2010 | Horan et al. | |
| 2010/0268264 A1 | 10/2010 | Bonnette et al. | |
| 2010/0286722 A1 | 11/2010 | Rizk et al. | |
| 2010/0305604 A1* | 12/2010 | Pah | A61F 2/013 606/200 |
| 2012/0245618 A1 | 9/2012 | Streeter et al. | |
| 2013/0006295 A1* | 1/2013 | Chanduszko | A61F 2/01 606/200 |
| 2013/0035717 A1 | 2/2013 | Belson | |
| 2013/0046330 A1* | 2/2013 | McIntosh | A61F 2/013 606/200 |
| 2013/0096606 A1* | 4/2013 | Bruchman | A61F 2/013 606/200 |

OTHER PUBLICATIONS

Alexandre F. Galio, Iduvirges L. Muller; Active Coatings: Examples and Applications; Bentham Science Publishers Ltd.; 2008; Rio Grande do Sul Federal University, pp. 68-71; Porto Alegre/RS, Brazil.

* cited by examiner

FLEXIBLE EMBOLIC DOUBLE FILTER

TECHNICAL FIELD

The present disclosure relates generally to devices and techniques for embolic protection, and relates more particularly to a filtration device with coarse and fine filters and a device body formed at least in part of an organic gel.

BACKGROUND

Embolic material can occur in the blood in human arteries and veins. Such embolic material may have the form of thrombus, lipid, lipoprotein, calcified material, and still others. Embolic material can cause a number of well-known problems in the human body, potentially blocking blood flow to critical organs and leading to heart attack, kidney failure or stroke. Various drug therapies are used to prevent or suppress the formation of certain types of emboli, and various interventional procedures are known for eliminating or treating conditions leading to the risk of creation or release of embolic material. Various treatments, and notably implanted medical devices, however, can themselves lead to the development and/or release of embolic material into the bloodstream.

In response to a perceived need to protect against the health risks relating to embolic material in the bloodstream, a number of designs and delivery techniques for devices such as vascular filters have been proposed. In one common strategy, a vascular filter is positioned in the vena cava to capture embolic material before the embolic material can enter the heart and be conveyed to the lungs, brain or elsewhere. Such devices have begun to find relatively widespread application. One embolic protection device is known from commonly owned U.S. patent application Ser. No. 12/038,238 to Hoffman. Hoffman discloses an embolic protection device for capturing emboli, having a frame and a Z-stent waistband. Exploiting flexibility of the waistband, the embolic protection device apparently is adjustable between a collapsed state, and an expanded state for capturing emboli. While Hoffman's design may work well, there is always room for improvement.

SUMMARY OF THE DISCLOSURE

In one aspect, an intraluminal filtration device for embolic protection includes a device body defining a longitudinal axis and having formed therein a central lumen extending longitudinally between a proximal body end and a distal body end. The device further includes a coarse filter located at the proximal body end and positioned to block larger-size particles from passing between the central lumen and a vessel lumen in a patient vessel receiving the filtration device. The device further includes a fine filter located at the distal body end and positioned to block smaller-size particles from passing between the central lumen and the vessel lumen. The device body further includes a body wall extending circumferentially around the longitudinal axis and including an outer surface, and an inner surface defining the central lumen. The body wall has a cylindrical shape and is formed at least in part of an organic gel.

In another aspect, a method for embolic protection includes positioning a filtration device within a vessel in a patient such that a coarse filter and a fine filter of the filtration device are positioned at upstream and downstream locations, respectively, within the patient vessel. The method further includes placing a cylindrical wall of the filtration device formed of an organic gel in contact with the patient vessel, such that the cylindrical wall is compliant with dilation and constriction thereof. The method further includes forming a fluid seal between the cylindrical wall and the patient vessel via the contact, such that fluid flowing through the patient vessel passes through a central lumen formed by the cylindrical wall and is filtered via each of the coarse and fine filters.

DETAILED DESCRIPTION

Figure 1:
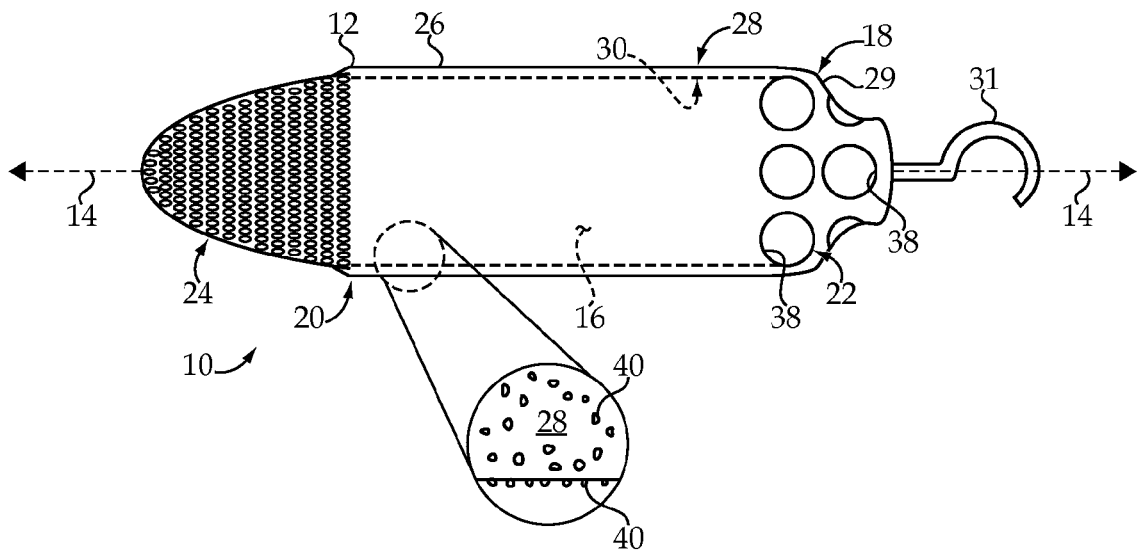
FIG. 1 is a side diagrammatic view, including a detailed enlargement, of a filtration device according to one embodiment.

Referring to FIG. 1, there is shown an intraluminal filtration device 10 for embolic protection, according to one embodiment. Device 10 includes a device body 12 defining a longitudinal axis 14 and having formed therein a central lumen 16 extending longitudinally between a proximal body end 18 and a distal body end 20. A coarse filter 22 is located at proximal body end 18 and positioned to block larger-size particles from passing between central lumen 16 and a vessel lumen in a patient vessel receiving device 10. A fine filter 24 is located at distal body end 20 and positioned to block smaller-size particles from passing between central lumen 16 and the vessel lumen. Device body 12 further includes a body wall 26 extending circumferentially around longitudinal axis 14. Body wall 26 includes an outer surface 28, and an inner surface 30 defining central lumen 16. Body wall 26 further has a cylindrical shape and is formed at least in part of an organic gel. By virtue of the construction and materials selected for filtration device 10, body wall 26 will typically be compliant with the patient vessel during dilation and constriction thereof. As will be further apparent from the following description, use of a relatively soft and compliant body wall, and for that matter compliance in the overall device body, provides a number of advantages with respect to service within a patient. In many instances, device 10 may be implanted within a patient for anywhere from several weeks to several months, and potentially even indefinitely, with the patient's body responding minimally to its presence.

In a practical implementation strategy, device 10 further includes a hook 31 positioned at proximal body end 18, and projecting in an axially outward direction from proximal end 18. Hook 31 enables retrieval of device 10 where desired via any of a number of known types of snare device. A shoulder 29 is formed upon device body 10 at proximal end 18, and provides for a sloping surface facilitating collapsing of device 10, and in particular body wall 12, when drawn into a sheath or the like for retrieval.

Also in a practical implementation strategy, fine filter 24 is formed of a textile and is shaped and attached to body wall 26 such that fine filter 24 radially deforms during the compliance of body wall 26. Fine filter 24 might be formed of material available under the trade name Dacron®, or any of a variety of other suitable polymeric materials. Embodiments are nevertheless contemplated where fine filter 24 is formed of a metallic material such as nitinol. In the illustrated embodiment, fine filter 24 has a dome shape and projects axially outward from distal body end 20, such that a peak of the dome can be understood to be intersected by longitudinal axis 14. Fine filter 24 may have a plurality of fine filter perforations 32 formed therein, and having diameters of about 0.1 millimeters, for example. Coarse filter 22 may be formed by a plurality of perforations 38 in device body 12, having diameters of about 0.5 millimeters, for example. As used herein, the term "about" should be understood in the context of conventional rounding to a consistent number of significant digits. Accordingly, about 0.01 would be understood to mean from 0.005 to 0.014, and so on. In a practical implementation strategy, device body 12 may be formed throughout by the organic gel material, and thus perforations 38 consist of holes through the organic gel material into an interior of device body 12 coextensive with lumen 16.

Figure 2:
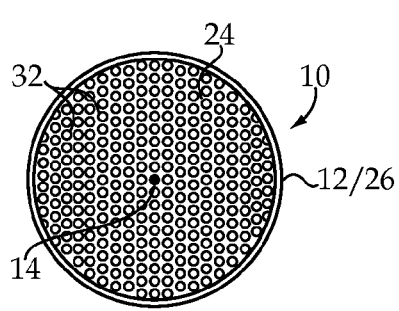
FIG. 2 is a first end view of the device of FIG. 1.
Figure 3:
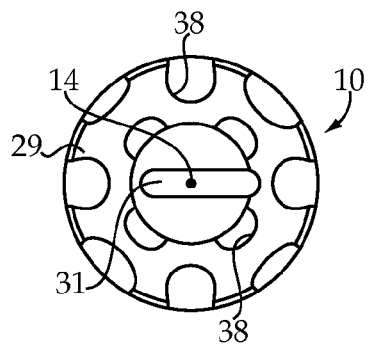
FIG. 3 is an opposite end view of the device of FIG. 1.

Referring also now to FIG. 2, there is shown an end view of device 10, illustrating fine filter 24, and body wall 26 just visible radially outward of fine filter 24. While central lumen 16 is not shown in FIG. 2, it will be understood that fine filter 24 has a radial extent substantially identical to central lumen 16, such that fine filter 24 might be thought of as forming a porous end wall of central lumen 16. In the illustrated embodiment, fine filter 24 is generally uniform circumferentially around axis 14. From FIG. 1 it can be noted that the dome shape of fine filter 24 is somewhat elongated such that a profile of fine filter 24 could be said to be partially oval in shape. Referring also now to FIG. 3 there is shown an end view of device 10, illustrating perforations 38 forming coarse filter 22. While perforations 38 are shown arranged in several rows and uniformly distributed within each of those rows, it should be appreciated that FIGS. 1 and 3 are purely illustrative, and perforations 38 might be arranged in any selected pattern, regular or irregular. Perforations 38 may be molded-in features, formed by a technician with a hand operated tool, or laser drilled, for instance. Also shown in FIG. 1 in a detailed enlargement are particulates 40 embedded in the organic gel material forming body wall 26 such that the particulates 40 protrude out from the organic gel material of wall 26, or otherwise impart a rough surface texture to outer surface 28. In a practical implementation strategy, particulates 40 may be calcium carbonate particulates mixed with the organic gel material forming body wall 26 prior to curing. In alternative embodiments particulates 40 could be incorporated to body wall 26 via another suitable technique, and could be formed of any other suitable bio-compatible material. The particulates 40 could be fibers of metal, organic or inorganic material.

Figure 4:
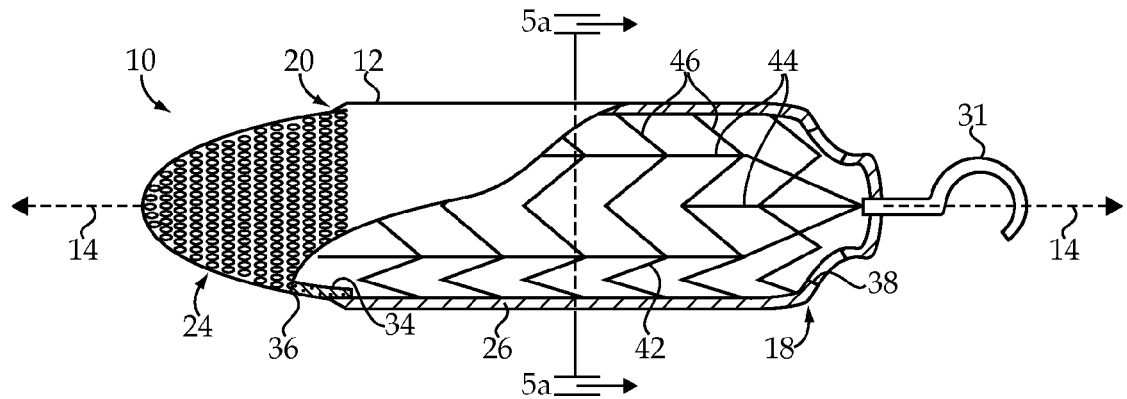
FIG. 4 is a partially sectioned side diagrammatic view of the device of FIG. 1.
Figure 5A:
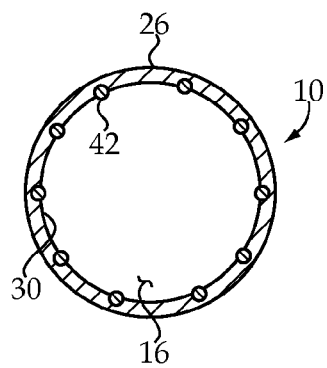
FIG. 5A is a sectioned view taken along line 5A-5A of FIG. 4.

Referring also now to FIG. 4, there is shown a partially sectioned side view of device 10. It can be seen from FIG. 4 that fine filter 24 has an inner filter surface 34 and an outer filter surface 36. Surfaces 34 and 36 may be substantially parallel and each form a similar dome shape to impart the overall dome shape to filter 24. As suggested above, body wall 26 may be radially compliant so as to expand and contract in radial directions as a patient vessel receiving device 10 dilates and constricts during ordinary blood pressure changes. The shape and attachment of fine filter 24 to body wall 26 may be such that filter 24 radially deforms during the compliance of body wall 26. Accordingly, the squeezing-down of the dome shape of fine filter 24 will be readily envisioned in conjunction with narrowing of the cylindrical shape of wall 26 during constriction of a patient vessel, as well as the reverse phenomena when the vessel dilates. A filter shaped as a flat disc may not likely have this capability; however, a pleated disc may be desirable. In the illustrated embodiment, the radial compliance of body wall 26 and the overall device 10 is enabled via a skeleton 42 attached to device body 12. Skeleton 42 may be formed of a second material different from the organic gel, and in many instances will be an endoskeleton formed of a non-biodegradable organic material or a metal. Retrieval hook 31 may be attached to skeleton 42, and could be formed of a metallic material such as stainless steel, for example, but could also be formed of polymeric materials. In the illustrated embodiment, skeleton 42 may have a plurality of longitudinal elements 44, and a plurality of latitudinal elements 46. Latitudinal elements 46 may each be formed into a so-called Z-configuration, such that skeleton 42 is amenable to elastic deformation. Referring also to FIG. 5A, there is shown a sectioned view along line 5A-5A, from which it will be apparent that skeleton 42 is embedded slightly into the organic gel material of body wall 26. Longitudinal elements 44 are illustrated in the sectioned view of FIG. 5A. Latitudinal elements 46 are omitted from the illustration for simplicity. While skeleton 42 is exposed to central lumen 16, it will be appreciated that a majority of the extent of lumen 16 is formed by wetted inner surface 30, and thus body wall 26 can be understood to define central lumen 16.

Figure 5B:
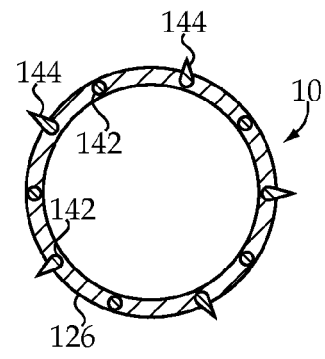
FIG. 5B is a sectioned view analogous to FIG. 5A, in a filtration device according to another embodiment.

Referring now to FIG. 5B, there is shown a sectioned view through a filtration device 110 according to a different embodiment. In device 110 two features different from that of device 10 are illustrated, namely, that a skeleton 142 is fully embedded in a body wall 126, rather than only partially embedded. Stated another way, body wall 126 encases skeleton 142 in device 110. Also shown in FIG. 5B are barbs or spicules 144 which are formed by protrusions of skeleton 142, or elements attached to skeleton 142, out of body wall 126. Spicules 144 serve a similar purpose to particulates 40 in device 10. In one practical implementation strategy spicules 144 might curve in an axial direction, into the page in FIG. 5B, or out of the page, to enhance retention or ease retrieval of device 110 depending upon its placement environment within a patient.

Figure 6:
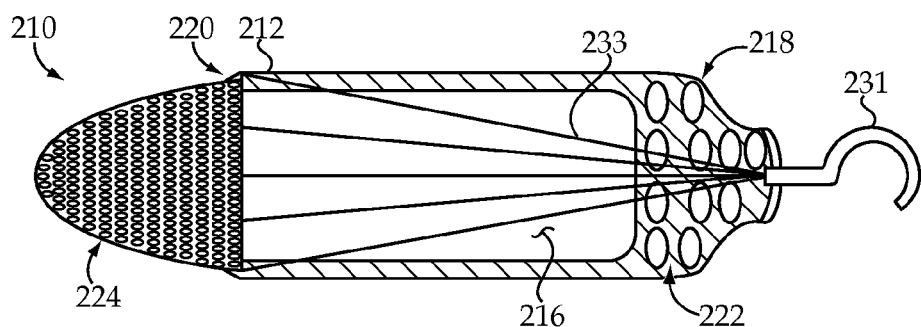
FIG. 6 is a partially sectioned side diagrammatic view of a filtration device, according to another embodiment.

Referring now to FIG. 6, there is shown an intraluminal filtration device 210 according to yet another embodiment. Device 210 includes a device body 212 having a proximal body end 218 and a distal body end 220, a coarse filter 222 at proximal body end 218 and a fine filter 224 at distal body end 220. A hook 231 is located at proximal body end 218. Device 210 is generally similar to foregoing embodiments, and constructed of similar materials such as an organic gel to form device body 212. Like the foregoing embodiments, filter 210, and in particular device body 212, will typically be radially compliant. Device 210 may further include at least one tensile-strengthening member 233 attached to device body 212 and extending between proximal and distal body ends 218 and 220 such that device body 212 is axially incompliant. In a practical implementation strategy, tensile-strengthening member 233 may include one of a plurality of non-metallic fibers, each attached to hook 231 and also to device body 212 at distal body end 220. Those skilled in the art will thus recognize that fibers 233 will have little or no effect on the radial compliance of device 210, but will serve to increase a tensile strength and stiffness, at least respecting axial lengthening of device 210. Accordingly, when hook 231 is snared to pull device 210 out of a patient, typically into a retrieval catheter, fibers 233 can reduce the risk of yielding the organic gel material forming device body 212 as hook 231 is being pulled upon. Members 233 may be arranged so as to themselves form a coarse filter, optionally the coarsest of three filters in device 210, or potentially the only coarse filter in a design where filter 222 is omitted. Members 233 might be arranged to define a pyramidal or roughly conical shape.

Those skilled in the art will also appreciate that skeletons 42 and 142 of the previous embodiments might also be understood to each include a plurality of tensile-strengthening members having similar properties. For instance, when hook 31 is being pulled on during retrieval of the device 10, longitudinal elements 44 can prevent yielding of the organic gel material forming device body 12, and in particular body wall 26. In still other instances designs are contemplated where it may be unnecessary to incorporate tensile-strengthening members at all. An organic gel body wall may itself have sufficient tensile strength for its intended applications that yielding of the organic gel material is not a concern. Higher durometer organic gel materials may be better suited for filtration devices made without tensile-strengthening members, whereas lower durometer organic gels may be more likely to be used where tensile-strengthening members are also part of the design, although the present disclosure is not thusly limited. In a practical implementation strategy, the organic gel material from which the device bodies are made as contemplated herein may have a Shore 00 hardness of about 30 or less at body temperature, and in some instances about 20 or less. Shore 00 hardness in the range of 0 to 80 are suitable for the gel material.

As noted above, materials from which filtration device 10 and the other devices contemplated herein are made may be non-biodegradable, and in general terms skeleton 42 and the organic gel from which device body 12 is made may be relatively inert, especially compared to metal materials. Skeleton 42 and the organic gel may also contain one or more drugs to further enhance inertness. Drug examples include GPIIb/IIIa inhibitors such as tirofiban, heparin, nitric oxide emitting compounds and thrombus lysing compounds such as plasmin or tissue plasminogen activator (TPA). The organic gel itself may be gelled polyethylene glycol diacrylate, polyvinyl alcohol, or other suitable gelled organics. Skeleton 42 may be formed of an organic material, potentially also a polyethelene glycol but typically having a higher durometer than the relatively low durometer organic gel.

In a practical implementation strategy, device 10 may be made by first constructing skeleton 42, and then covering skeleton 42 by spraying or dipping skeleton 42 into polymer coating material to be cured for forming cylindrical wall 26 and optionally other parts of device 10. Electrospinning the polymer coating material may also be utilized. The skeleton itself may be formed of a metallic spring material such as nitinol or stainless steel having the Z-configuration or a similar configuration as shown in the drawings, but in a practical implementation strategy will be a polymeric material as noted above. A network of wound or electrospun polymer fibers might also be used to form the individual elements of skeleton 42. Alternatively, the organic gel could be molded around the preformed skeleton. The organic gel may then be cured by solvent evaporation, chemical catalysis, or via cross linking with light, electron beam or gamma radiation. Drugs could be incorporated into skeleton 42 or the organic gel material before or during forming the organic gel device body. As noted above, embodiments are contemplated where no skeleton is used at all and the filtration device is essentially a cylinder of organic gel with the coarse and fine filters, where the coarse filter might also be formed of the organic gel. The term "organic gel" is meant to include silicone gel.

With respect to the embodiment of FIG. 6, a similar construction strategy might be used, with a suitable mechanism used to hold fibers 233 generally in a conical configuration as shown in FIG. 6, attached to hook 231, and then having the organic gel molded into shape. In still other instances, rather than the fibers oriented and extending as they are shown in FIG. 6, other embodiments might include polymeric fibers oriented longitudinally and entirely or predominantly within organic gel material forming the device body. Tensile-strengthening of the device would thus be achieved by way of such longitudinally oriented fibers. The length of such fibers could be equal to the length of a body wall formed of organic gel, but also could potentially be shorter in which case the number of fibers would likely be greater at least inversely proportional to their length. In other words, for a given number of long fibers spanning a full length of the cylindrical wall of organic gel, an alternative design using shorter fibers would typically have a greater number of fibers in inverse proportion to their length. Longitudinal fibers embedded within a cylindrical organic gel wall could even be considered an advantageous design where greater axial force to remove a filter from a blood vessel is anticipated.

INDUSTRIAL APPLICABILITY

Figure 7:
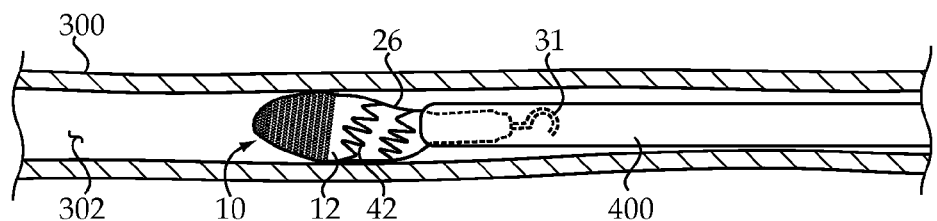
FIG. 7 is a side diagrammatic view at one stage of a procedure, according to one embodiment.

Referring to the drawings generally, but in particular now to FIG. 7, there is shown device 10 as it might appear being initially positioned within a vessel 300 in a patient, and having been pushed partially out of a delivery catheter 400 so that device body 12 is extending out of catheter 400 and beginning to come into contact with an inner wall of vessel 300 within a vessel lumen 302. Skeleton 42 is expanding from an elastically deformed state towards a relaxed or rest state at which cylindrical wall 26 will be placed in contact with the inner wall of patient vessel 300 to form a fluid seal between wall 26 and the patient vessel via the contact. An elongate pushing tool or the like (not shown) may be passed through catheter 400 and used to push against hook 31 to assist in deploying device 10 within vessel lumen 302. Device 10 will typically be positioned such that coarse filter 22 is positioned at an upstream location and fine filter 24 is positioned at a downstream location, within patient vessel 300. Fluid flowing through the patient vessel may thus pass through central lumen 16 and be filtered via each of coarse filter 22 and fine filter 24. In the illustrated embodiment, pushing device 10 out of catheter 400 may be understood as relieving radial compressive force on device 10 during its placement, allowing elastically deformed skeleton 42 to responsively urge wall 26 into contact with patient vessel 300. The elastic properties of skeleton 42 will assist in compliance of device 10 with the vessel, such as during dilation and constriction. In the case of an embodiment having spicules, barbs, or particulates as described herein, device 10 may be retained within the patient vessel once positioned via the assistance of such retention elements protruding out from cylindrical wall 26.

Figure 8:
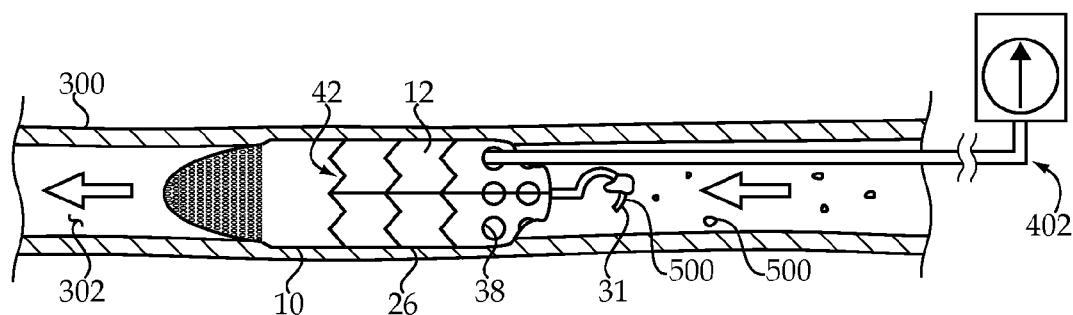
FIG. 8 is a side diagrammatic view at another stage of the procedure.

Referring now to FIG. 8, there is shown device 10 as it might appear having been deployed, catheter 400 removed, and filtering of larger-size particles via filter 38 and smaller-size particles via filter 24 commenced. Particles 500 are shown carried through lumen 302, with a direction of flow shown via arrows. It can be noted that a large, flap-like particle is in contact with hook 31. In many instances, hook 31 can provide for an additional surface exposed to fluid so that certain potentially problematic and occlusive embolic particles may in fact be caught on hook 31 rather than obscuring any of perforations 38. Also shown in FIG. 8 is a vacuum mechanism 402 having been percutaneously advanced through lumen 302, and into one of perforations 38. The spicules or barbs may be oriented to point distally, but be shaped so that a curve of the barb bears against the sheath. This configuration may facilitate sliding against the sheath, but retain the ability of the distal tip of the barb to engage the vessel wall. Device 10 may be well-suited to cleaning in vivo, with devices being known and available which are small enough for feeding through perforations 38, and all the way into contact or nearly into contact with filter 24 to remove accumulated embolic particles and therefore extend the service life of device 10.

Figure 9:
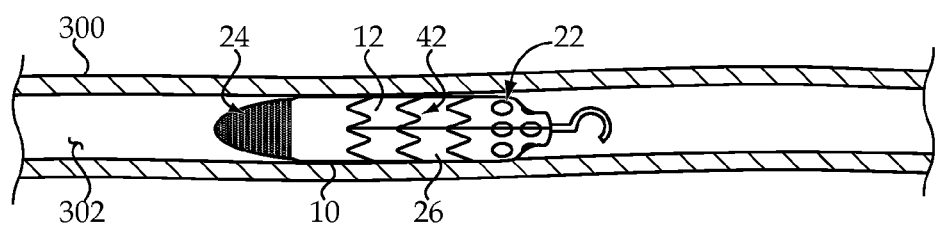
FIG. 9 is a side diagrammatic view of a filtration device positioned for service within a patient.
Figure 10:
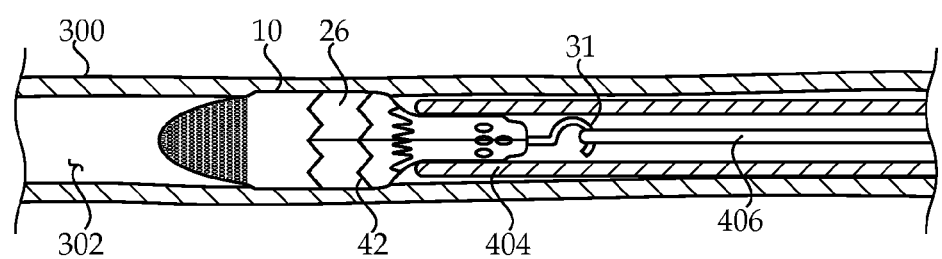
FIG. 10 is a side diagrammatic view at another stage of the procedure.

Referring also now to FIG. 9, there is shown device 10 within lumen 302, and having been radially compressed or condensed relative to the state depicted in FIG. 8. It will be recalled that device 10 may be radially compliant with vessel 300, and may expand and contract with normal blood pressure cycles of the patient. Referring to FIG. 10, there is shown a retrieval catheter 404 positioned part-way over device 10, and a snare or the like 406 having been advanced through catheter 404 to engage hook 31. It will be appreciated that retrieval of device 10 may include stepwise pulling of device 10 into retrieval catheter 404 via snare 406 combined with stepwise and alternating pushing of catheter 404 over device body 12. In this general manner, a clinician can work device 10 gradually into retrieval catheter 404, minimizing disturbance to the endothelial layer within vessel 300. Device 10 can then be withdrawn from the patient within retrieval catheter 404.

In a practical implementation strategy, intraluminal device 10, and the other devices contemplated herein, may be used to filter blood in many different body vessels. Positioning within the aortic arch, within a cranial artery, a carotid artery, the vena cava, and still other locations are contemplated herein. As discussed above, device 10 and the other devices contemplated herein may also be positioned for service for a relatively extended length of time, potentially weeks or several months or even indefinitely. The combination of the flexibility and softness of the materials and construction of device 10 can enable device 10 to reside within the patient's body almost as if it were not there, minimally disturbing the delicate endothelial layer within the patient's body lumen or on the device 10, and being generally inert to biological activity such as might lead to generation of embolic material or other problems.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. Other aspects, features and advantages will be apparent upon an examination of the attached drawings and appended claims.

What is claimed is:

1. An intraluminal filtration device for embolic protection comprising:
    a device body defining a longitudinal axis and having formed therein a central lumen extending longitudinally between a proximal body end and a distal body end;
    a coarse filter located at the proximal body end and positioned to block larger-size particles from passing between the central lumen and a vessel lumen in a patient vessel receiving the filtration device;
    a fine filter located at the distal body end to form a porous end wall of the central lumen that is intersected by the longitudinal axis and position to block smaller-size particles from passing between the central lumen and the vessel lumen;
    the device body further including a body wall formed of an organic gel to include an inner surface defining an inner cylinder and an outer surface defining an outer cylinder extending circumferentially around and along the longitudinal axis from the proximal body end to the distal body end; and
    wherein the body wall is radially compliant, and further comprising at least one tensile-strengthening member attached to the device body and extending between the proximal and distal body ends such that the device body is axially incompliant.

2. The device of claim 1 wherein the fine filter includes a textile and is shaped and attached to the body wall such that the fine filter radially deforms during compliance of the body wall with the patient vessel during dilation and constriction thereof.

3. The device of claim 2 wherein the fine filter has a dome shape and projects axially outward from the distal body end.

4. The device of claim 2 wherein the coarse filter includes a plurality of perforations defined by the device body.

5. The device of claim 1 wherein the at least one tensile-strengthening member includes one of a plurality of non-metallic fibers.

6. The device of claim 1 further comprising a skeleton attached to the device body and formed of a second material different from the organic gel.

7. The device of claim 6 wherein the device body is formed throughout of the organic gel, and the organic gel has a Shore 00 hardness of about 30 or less.

8. The device of claim 7 wherein the skeleton includes an endoskeleton and the second material is a non-biodegradable organic material.

9. The device of claim 7 further comprising a retrieval hook attached to the skeleton.

10. A method for embolic protection with an intraluminal filtration device that includes a device body defining a longitudinal axis and having formed therein a central lumen extending longitudinally between a proximal body end and a distal body end; a coarse filter located at the proximal body end and positioned to block larger-size particles from passing between the central lumen and a vessel lumen in a patient vessel receiving the filtration device; a fine filter located at the distal body end to form a porous end wall of the central lumen that is intersected by the longitudinal axis and positioned to block smaller-size particles from passing between the central lumen and the vessel lumen; and the device body further including a body wall formed of an organic gel to include an inner surface defining an inner cylinder and an outer surface defining an outer cylinder extending circumferentially around and along the longitudinal axis from the proximal body end to the distal body end, wherein the body wall is radially compliant, and further comprising at least one tensile-strengthening member attached to the device body and extending between the proximal and distal body ends such that the device body is axially incompliant, the method comprising the steps of:

positioning the filtration device within the vessel in the patient such that the coarse filter and the fine filter of the filtration device are positioned at upstream and downstream locations, respectively, within the patient vessel;

placing the body wall of the filtration device formed of the organic gel in contact with the patient vessel; and forming a fluid seal between the cylindrical wall and the patient vessel via the contact, such that fluid flowing through the patient vessel passes through the central lumen formed by the cylindrical wall and is filtered via each of the coarse and fine filters.

11. The method of claim 10 further comprising a step of relieving radial compressive force on the filtration device during the placement of the cylindrical wall, such that an elastically deformed skeleton of the filtration device responsively urges the cylindrical wall into contact with the patient vessel.

12. The method of claim 11 wherein the skeleton is formed of a non-biodegradable organic material.

13. The method of claim 11 further comprising a step of retaining the filtration device within the patient vessel once positioned, via retention elements protruding out from the cylindrical wall.

14. The method of claim 10 wherein the filtering includes filtering larger-size particles from the fluid via perforations forming the coarse filter in the device body of the filtration device.

15. The method of claim 14 wherein the device body is formed of the organic gel throughout.

16. The method of claim 14 wherein the filtering includes filtering the smaller-size particles via a textile attached to the device body and forming the fine filter.

17. The method of claim 10 further comprising a step of cleaning the filtration device of accumulated embolic particles.

* * * * *